(12) United States Patent
Thompson (10) Patent No.: US 6,580,947 B1
(45) Date of Patent: Jun. 17, 2003

(54) MAGNETIC FIELD SENSOR FOR AN IMPLANTABLE MEDICAL DEVICE

(75) Inventor: David L. Thompson, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/523,674

(22) Filed: Mar. 10, 2000

(51) Int. Cl.$^7$ ................................................ A61N 1/40
(52) U.S. Cl. ............................ 607/30; 607/32; 607/60
(58) Field of Search .......................... 607/30, 32, 59, 607/60, 1, 2, 36

(56) References Cited

U.S. PATENT DOCUMENTS

| | | | |
|---|---|---|---|
| 4,301,804 A | 11/1981 | Thompson et al. | 128/419 |
| 4,541,431 A | 9/1985 | Ibrahim et al. | 128/419 |
| 4,611,127 A | 9/1986 | Ibrahim et al. | 307/116 |
| 5,161,540 A | 11/1992 | Mueller | 128/695 |
| 5,374,792 A | 12/1994 | Ghezzo et al. | 200/16 |
| 5,391,188 A | 2/1995 | Nelson et al. | 607/9 |
| 5,438,990 A | 8/1995 | Wahlstrand et al. | 128/653.1 |
| 5,454,904 A | 10/1995 | Ghezzo et al. | 216/13 |
| 5,475,353 A | 12/1995 | Roshen et al. | 335/78 |
| 5,563,344 A | 10/1996 | Kaiser et al. | 73/514.24 |
| 5,594,331 A | 1/1997 | White et al. | 324/117 |
| 5,694,952 A | 12/1997 | Lidman et al. | 128/899 |
| 5,722,998 A | 3/1998 | Prutchi et al. | 607/30 |
| 5,771,902 A | 6/1998 | Lee et al. | 128/897 |
| 5,778,513 A | 7/1998 | Miu et al. | 29/602.1 |
| 5,801,533 A | 9/1998 | Kalb, Jr. | 324/252 |
| 5,914,507 A | 6/1999 | Polla et al. | 257/254 |
| 5,954,758 A | 9/1999 | Peckham et al. | 607/48 |
| 5,994,816 A | 11/1999 | Dhuler et al. | 310/307 |
| 5,994,880 A | 11/1999 | Dropps | 320/140 |

OTHER PUBLICATIONS

Kovacs et al., "Bulk Micromachining of Silicon," Proceedings of The IEEE, vol. 86, No. 8, Aug. 1998.

Primary Examiner—George R. Evanisko
Assistant Examiner—Roderick Bradford
(74) Attorney, Agent, or Firm—Girma Wolde-Michael (57) ABSTRACT

An implantable medical device (IMD) uses a solid-state sensor for detecting the application of an external magnetic field, the sensor comprises one or more magnetic field responsive microelectromechanical (MEM) switch fabricated in an IC coupled to a switch signal processing circuit of the IC that periodically determines the state of each MEM. The MEM switch comprises a moveable contact suspended over a fixed contact by a suspension member such that the MEM switch contacts are either normally open or normally closed. A ferromagnetic layer is formed on the suspension member, and the suspended contact is attracted or repelled toward or away from the fixed contact. The ferromagnetic layer, the characteristics of the suspension member, and the spacing of the switch contacts may be tailored to make the switch contacts close (or open) in response to a threshold magnetic field strength and/or polarity. A plurality of such magnetically actuated MEM switches are provided to cause the IMD to change operating mode or a parameter value and to enable or effect programming and uplink telemetry functions.

18 Claims, 5 Drawing Sheets

MAGNETIC FIELD SENSOR FOR AN IMPLANTABLE MEDICAL DEVICE

FIELD OF THE INVENTION

The present invention relates generally to the field of implantable medical devices, and more particularly to an implantable medical device (IMD) which incorporates one or more microelectromechanical (MEM) magnetic field sensor that switches between open and closed states in response to the application of a magnetic field against the patient's skin over the IMD.

BACKGROUND OF THE INVENTION

In the field of IMDs that are implanted within the body of a human patient, such as implantable cardiac pacemakers and implantable cardioverterdefibrillators (ICDs) and the like, it is often desirable that certain operational modes and parameters of the device be altered temporarily or chronically in a non-invasive (i.e. non-surgical) manner. One of the most common methods of non-invasive alteration of operational parameters employs a miniaturized reed switch contained within the IMD housing that responds to the application of a magnetic field against the patient's skin over the IMD, e.g., by closing switch contacts, for as long as the magnetic field persists.

The typical magnetic reed switch consists of a hermetically sealed cylindrical encapsulation housing two metallic reeds. The metallic reeds are disposed within the encapsulation such that when a sufficiently strong magnetic force is applied to the IMD from outside the patient's body, the magnetic force draws the two reeds into electrical contact with one another, thereby completing an electrical circuit. When the magnetic field is withdrawn, the reeds separate, breaking the electrical circuit. Such an arrangement is disclosed, for example, in commonly assigned U.S. Pat. Nos. 3,805,796, 3,920,005, and 4,066,086.

Such miniaturized reed switches were first incorporated into implantable pulse generators (IPGs) of pacemakers. Reed switch closure is used in the context of demand pacemaker IPGs to switch the pacing mode to a fixed rate or asynchronous mode for follow-up and trans-telephonic evaluation of the implanted pacemaker. In addition, pacing rate, pacing pulse width, and mode changes which occur upon reed switch closure are used to indicate device function and battery status. One use of this technique was to monitor impending battery depletion through observation of a change in the pacing rate from a preset or programmed pacing rate in response to a battery voltage drop, as described, for example, in U.S. Pat. No. 4,445,512. This approach could only provide a low bandpass data channel, of course, to avoid interfering with the primary function of pacing the patient's heart when necessary.

As digital circuit technology advanced, it was recognized that control of operating modes and parameters of implanted medical devices could be realized in digital or binary circuits employing memorized control states or operating parameter values. In order to change an operating mode or parameter value, "programmers" were developed based on radio frequency (RF) downlink data communication from an external programmer transceiver to a telemetry transceiver and memory incorporated within the IMD. Through the use of such telemetry systems, it became possible to provide uplink data telemetry to transmit the contents of a register or memory within the IMD to the telemetry receiver within the programmer employing the same RF transmission capabilities. The magnetically actuated reed switch was required to be closed by an externally applied magnetic field to enable the IPG to respond to simultaneously transmitted downlink telemetry signals to ensure that the IPG telemetry receiver would not mistakenly respond to RF EMI to which the patient might be exposed. Although a variety of programming schemes have been proposed that eliminate the requirement for the externally applied magnetic field and the reed switch closure, most IMDs and RF telemetry systems continue to employ them.

Pacemaker and ICD IPGs and other IMDs are continually being made smaller and smaller while retaining and even increasing device longevity and operating functions. Reed switches are typically the only devices with moving parts in such IMD housings, theoretically making them more susceptible than the pacemaker's electronic components to damage or mechanical failure such as might result from vibration or mechanical shock or handling during assembly of the IMD. It is difficult to miniaturize reed switches while retaining high reliability and integrity as well as sufficient sensitivity to be responsive only to predetermined magnetic field intensities and not respond to weaker magnetic fields that the patient may encounter from other electromagnetic devices or systems While a reed switch must be sensitive enough to be responsive to a particular externally applied magnetic field, it is important that the switch not be so sensitive that it is responsive to every magnetic field to which the patient may be exposed in daily activity. As a result, the manufacturing tolerances for reed switches are low, making manufacturing costs high.

A number of alternative devices have been proposed to overcome the disadvantages of a reed switch. Commonly assigned U.S. Pat. No. 4,301,804 discloses a pacemaker IPG in which a circuit produces a strobe signal which is used to turn on a current flow through a Hall effect element once each pacemaker pulse cycle for a selected period of time. The presence of an external magnetic field alters the electrical properties of the Hall effect element (typically implemented in a bipolar integrated circuit fabrication process), so that a positive voltage is provided to the pacemaker circuitry when the element is strobed. While the Hall effect element is not a mechanical device, and is in that respect preferable to a reed switch, the Hall effect element has proven to be less sensitive than a reed switch, requires expensive processing and unique, expensive packaging, and is not compatible with standard linear CMOS processing which is preferentially used in implantable medical devices.

As an alternative to using mechanical reed-switches or Hall effect elements to detect and measure magnetic fields, it has been proposed in commonly assigned U.S. Pat. Nos. 5,438,990, 5,292,342, 5,391,188, and 5,891,180, for example, to employ split-drain field-effect transistors, sometimes called MAGFETs, for this purpose. Although similar to a conventional field-effect transistor (FET), the drain of a MAGFET is split into two isolated halves. Application of a magnetic field to a MAGFET device gives rise to a differential in the currents in the two split-drain-halves, the extent of this differential being directly proportional to the strength of the applied magnetic field.

Although MAGFETs, like Hall-effect devices, have the advantage of being solid-state devices, some problems with use of Hall-effect and MAGFETs are known. Unlike classic reed switches, the MAGFETs and Hall-effect devices draw electrical power when operating in response to a strobe signal. More complex circuitry is required as set forth in the above-referenced '770 patent to process the MAGFET signal to provide adequate sensitivity and to compensate for leakage and drift, than is required to process a simple reed switch signal. The classic reed switch, while overly large, has the advantage of being more consistent in operating characteristics and sensitivity to applied magnetic fields and requires no applied power and much less signal processing circuitry.

A need therefore exists for magnetic field responsive switch that mimics these favorable characteristics of the reed switch and can be greatly miniaturized and be readily incorporated into an IMD.

SUMMARY OF THE INVENTION

In accordance with the present invention, one or more magnetic field responsive MEM switch is substituted for the reed switch, MAGFET or Hall effect devices described above currently used or proposed for use in IMDs. In accordance with the present invention, two or more MEM switches can be provided that selectively respond to externally applied north (N) and south (S) polarity fields and/or to differing magnetic field strengths to generate separate single or multiple switch closed signals that cause the IMD to selectively respond and operate in separate prescribed operating modes.

The MEM switch comprises a moveable contact suspended over a fixed contact by a suspension member such that the MEM switch contacts are either normally open or normally closed. A ferromagnetic layer is formed on the suspension member, and the suspended contact is attracted or repelled toward or away from the fixed contact. The ferromagnetic layer, the characteristics of the suspension member, and the spacing of the switch contacts may be tailored to make the switch contacts close (or open) in response to a threshold magnetic field strength and/or polarity. A plurality of such magnetically actuated MEM switches are provided to cause the IMD to change operating mode or a parameter value and to enable or effect programming and uplink telemetry functions.

An IMD control and timing circuit establishes IMD operating modes in accordance with programmed operating mode and parameter value commands. The IMD control and timing circuit responds to a switch signal to effect a programmed operating mode or parameter value. A number of programming and interrogation functions may be accomplished selectively when a plurality of such magnetically actuated MEM switches each selectively responsive to applied external magnetic field strengths and/or polarities are incorporated into IMD circuitry The magnetically actuated MEM switch offers a number of advantages. In one approach, semiconductor batch fabrication techniques are employed to achieve what is in effect three-dimensional micromachining of single-crystal and polycrystalline silicon and silicon dielectrics separately or on a common substrate with other IMD circuitry to form one or more magnetically actuated MEM switch. Manufacturing and assembly are simplified and cost is lowered. The resulting magnetically actuated MEM switch or switches are small, rugged, simple, and can be interfaced with simple switch processing circuitry. The magnetically actuated MEM switch and the simple switch processing circuitry coupled thereto lowers current drain in comparison to the very little current in comparison to the reed switch, MAGFET or Hall effect devices and the circuitry coupled therewith.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS OF THE INVENTION

Figure 1:
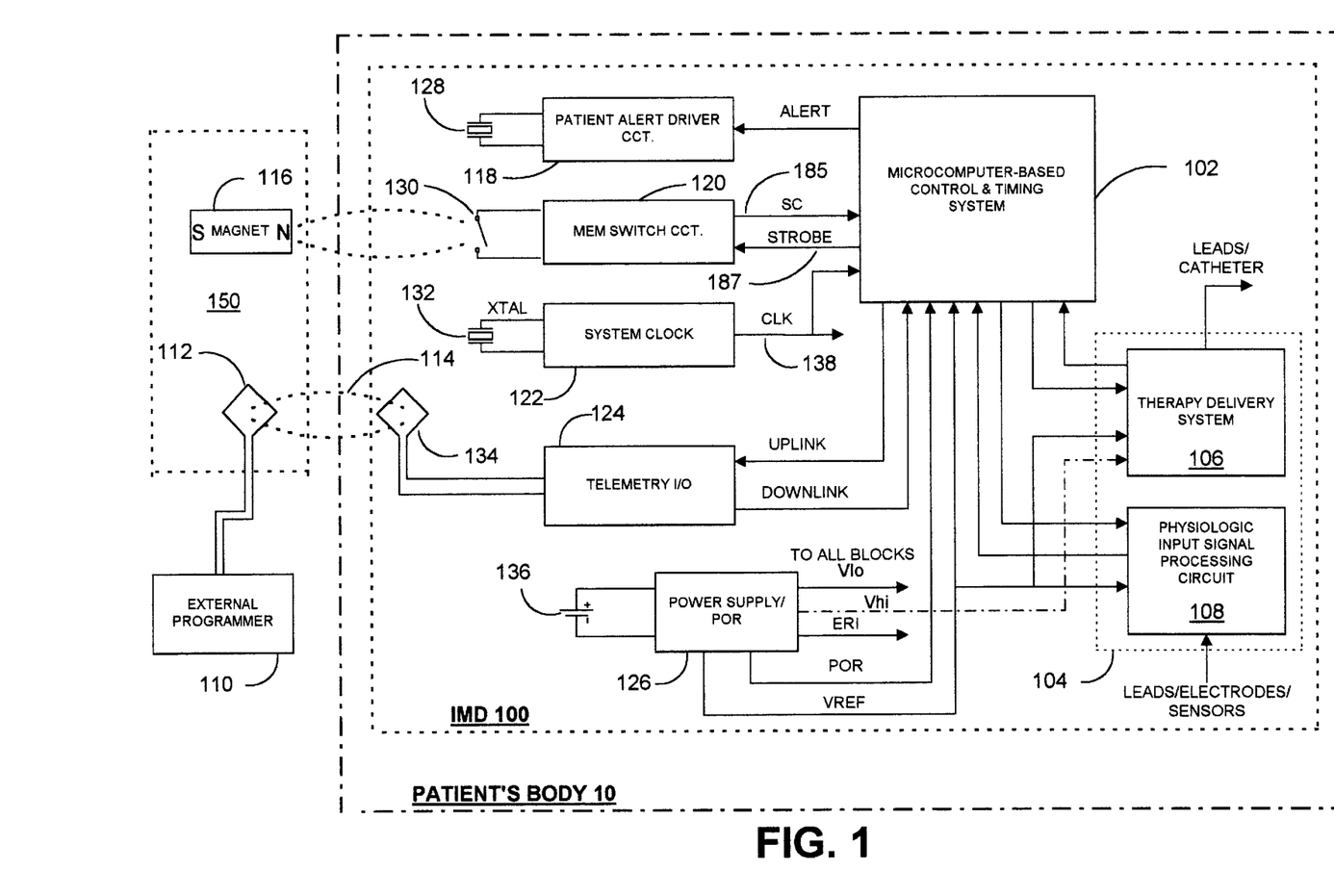
FIG. 1 is a block diagram of a system architecture of an exemplary IMD that incorporates delivery of a therapy and/or physiologic input signal processing in which magnetic field responsive MEMs are incorporated in accordance with the present invention.

The preferred embodiments of the present invention disclose uses of one or more magnetic field responsive MEM switch especially fabricated to respond to externally applied magnetic fields in preference to the above-described reed switches, Hall effect switches, and MAGFET circuits in IMD system architectures of the type depicted in FIG. 1. The closure of the MEM switch or switches induces a temporary change in operating mode or parameter values for therapeutic or diagnostic purposes and to enable downlink RF telemetry reception and uplink telemetry transmission. An implantable pacing system incorporated into a pacemaker IPG or ICD IPG 200 is described below in reference to FIG. 2. The present invention may also be implemented in simplified, low cost pacing IPG operating system of the type described in the above-referenced '180 patent. In that system, pacing modes and parameter values are programmed and uplink transmission of IMD information is triggered using the timed application and removal of a permanent magnet over the implantation site.

FIG. 1 depicts a system architecture of an exemplary IMD 100 implanted into a patient's body 10 that provides delivery of a therapy and/or physiologic input signal processing in which operating modes and parameter values can be temporarily changed by application of a magnetic field and/or telemetry enabled in accordance with the present invention using one or more magnetically actuated MEM switch 130. The typical IMD 100 has a system architecture that is constructed about a microcomputer-based control and timing system 102 which varies in sophistication and complexity depending upon the type and functional features incorporated therein. The functions of microcomputer-based IMD control and timing system 102 are controlled by firmware and programmed software algorithms stored in RAM and ROM including PROM and EEPROM and are carried out using a CPU, ALU, etc., of a typical microprocessor core architecture. The microcomputer-based IMD control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. It will also be understood that control and timing of IMD 100 can be accomplished with dedicated circuit hardware as described, for example, in the above-referenced '188 and '342 patents, or state machine logic rather than a programmed micro-computer.

The IMD 100 also typically includes patient interface circuitry 104 for receiving signals from sensors or electrodes located at specific sites of a patient's body 10 and/or delivering a therapy to a site of the patient's body. The typical patient interface circuitry 104 therefore comprises a therapy delivery system 106 and/or a physiologic input signal processing circuit 108 or simply one or the other.

The physiologic input signal processing circuit 108 is coupled to electrodes and/or physiologic sensors on or in the housing of the IMD 100 or situated at sites distanced from the IMD housing, typically in distal portions of elongated leads. In the latter case, physiologic signals developed by such sensors or traversing the electrodes are coupled by way of elongated leads or catheters or transmitted through the body to physiologic input signal processing circuit 108.

The IMD 100 can comprise an implantable cardiac monitor without a therapy delivery system 106, e.g., an implantable EGM monitor for recording the cardiac electrogram from electrodes remote from the heart as disclosed in commonly assigned U.S. Pat. No. 5,331,966 and PCT publication WO 98/02209. Or the IMD 100 can comprise an implantable hemodynamic monitor (IHM) for recording cardiac electrogram and other physiologic sensor derived signals, e.g., one or more of blood pressure, blood gases, temperature, electrical impedance of the heart and/or chest, and patient activity. The Medtronic® REVEAL® Insertable Loop Recorder having spaced housing EGM electrodes is an example of the former, and the Medtronic® CHRONICLE® IHM coupled with a capacitive pressure and temperature sensing lead and EGM sense electrodes of the type described in commonly assigned U.S. Pat. No. 5,564,434 is an example of the latter.

In these monitor embodiments, physiologic data, e.g., the cardiac EGM and/or sensor derived data is typically stored in RAM in microcomputer-based control and timing system 102 for uplink telemetry to an external programmer 110 when the IMD 100 receives a downlink telemetered interrogation command from the programmer 110. The data storage is either triggered by a timer of the IMD 100 on a periodic basis or by detection logic within the physiologic input signal processing circuit 108 upon satisfaction of certain event detection criteria. In some cases, the patient is provided with a magnet 116 or simplified external programmer 110, e.g., a patient activator, that can be applied over the subcutaneously implanted IMD 100 to trigger physiologic data storage when the patient experiences certain symptoms.

In either case, event related data, e.g., the date and time, may be stored along with the stored episode data for uplink telemetry in a later interrogation session.

Therapy delivery IMDs 100 include the therapy delivery system 106 that can take a variety of forms and typically involve delivering electrical stimulation to body muscle groups, the heart, the brain, other organs, selected nerves, and the spinal column or the delivery of drugs into organs for therapeutic treatment or into the spinal column for pain relief. It will be understood that most of these therapy delivery IMDs also have a physiologic input signal processing circuit 108 that processes physiologic signals that are used to trigger or modulate therapy delivery and are stored as physiologic signal data for later retrieval as described above.

With respect to therapy delivery device configurations, the IMD 100 and therapy delivery system 106 may be configured to operate an implantable heart assist device or pump implanted in patients awaiting a heart transplant operation. In this case, derived relative blood pressure and/or temperature values may be used to modulate the action of the pump to maintain adequate cardiac output. The IMD 100 and therapy delivery system 106 may also be configured as a cardiomyostimulator to stimulate a muscle surgically wrapped about the heart in synchrony with cardiac depolarizations to increase cardiac output of a diseased heart.

The IMD 100 and therapy delivery system 106 may be configured to include a substance delivery apparatus or pump which is coupled to a suitable catheter extending to a site of the patient's body to deliver a substance, e.g., a therapeutic or diagnostic agent or drug, from a substance reservoir. For example, a drug to treat hypertension may be delivered to the patient's heart or vascular system, or an analgesic may be delivered to the spinal column to relieve intractable pain.

Or IMD 100 may be configured as a cardiac stimulator for sensing cardiac signals and delivering pacing pulses or cardioversion/defibrillation shocks to the heart through therapy delivery system 106. The IMD 100 may include any one or a combination of an anti-tachycardia pacer, anti-bradycardia pacer, cardioverter and/or defibrillator having suitable leads and electrodes extending to the patient's heart as part of the IMD therapy delivery system 106.

Similarly, the IMD 100 and therapy delivery system 106 may be configured with appropriate lead borne electrodes as a deep brain stimulator to control Parkinson's disease, or as a spinal column stimulator or nerve stimulator to control pain. The IMD and therapy delivery system 106 may be configured with appropriate electrodes and/or sensors to detect cardiac ischemia and provide compensatory autonomous nerve stimulation.

The IMD 100, therapy delivery system 106, and physiologic input signal processing circuit 108 may also be configured as a cochlear implant responding to sensor sound transducer inputs and providing stimulation to the cochlea.

These are merely exemplary configurations of IMD 100, therapy delivery system 106, and physiologic input signal processing circuit 108 for therapy delivery and/or monitoring. In all cases, the micro-computerbased control and timing system 102 governs all operating functions employing an appropriate, programmable operating algorithm. FIG. 1 also depicts other typical components common to an IMD 100 in any of these therapy delivery and/or monitoring configurations.

For example, most such IMDs have programmable operating modes and parameters that are stored in RAM in the microcomputer-based control and timing system 102. The operating modes and parameter values can be remotely programmed using the external programmer 110 to transmit commands and values in a downlink telemetry link 114 between external telemetry antenna 112 and IMD telemetry antenna 134 and received and decoded in the telemetry I/O circuit 124 in a manner well known in the art.

All current IMDs rely upon a source of electrical energy to power the IMD operating system including the circuitry of IMD 100 and to power any electromechanical devices, e.g., valves, pumps, etc. of a substance delivery IMD or to provide electrical stimulation energy of an ICD shock generator, cardiac pacing pulse generator or other electrical stimulation generator. The typical energy source is a high energy density, low voltage battery 136 coupled with a power supply/POR circuit 126 having power-on-reset (POR) capability. The power supply/POR circuit 126 provides one or more low voltage power Vlo, the POR signal, one or more VREF sources, current sources, an elective replacement indicator (ERI) signal, and, in the case of an ICD, high voltage power Vhi to the therapy delivery system 106. Not all of the conventional interconnections of these voltages and signals are shown in FIG. 1.

In addition, in certain IMDs, an audible patient alert warning or message is generated by a transducer 128 when driven by a patient alert driver 118 to advise of device operations, battery power level or a monitored patient condition. In ICDs, the patient may be warned of the detection of a malignant tachyarrhythmia and the imminent delivery of a cardioversion/defibrillation shock to enable the patient to assume a resting position prior to delivery.

Virtually all current electronic IMD circuitry employs docked CMOS digital logic ICs that require a clock signal CLK provided by a piezoelectric crystal 132 and system clock 122 coupled thereto. In FIG. 1, each CLK signal generated by system clock 122 is routed to all applicable docked logic via a dock tree 138. The system clock 122 provides one or more fixed frequency CLK signal that is independent of the battery voltage over an operating battery voltage range for system timing and control functions and in formatting uplink telemetry signal transmissions in the telemetry I/O circuit 124.

Figure 2:
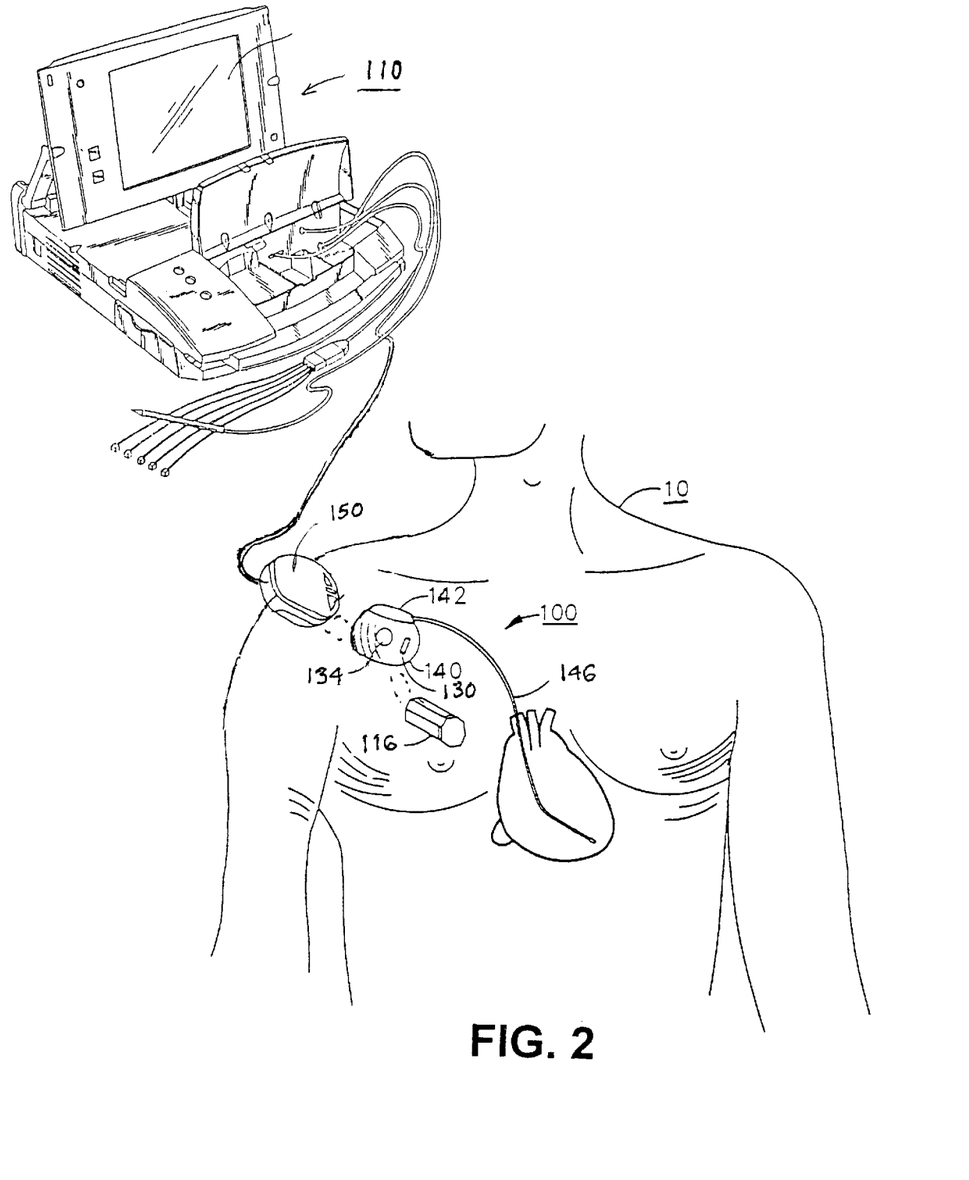
FIG. 2 is a simplified schematic view of the application of magnetic fields to an exemplary IMD, specifically a pacemaker IPG in this illustration, implanted in a patient's body in the course of a telemetry session or initiation of a temporary change in operating mode or parameter value

In FIG. 2, the IMD 100 is illustrated as a cardiac pacemaker implanted within the patient's body 10 comprising a pacemaker IPG 140 and a pacing lead 146 which extends from the IPG connector 142 to one or more pace/sense electrodes located in or on the patients atrium or ventricle in the conventional manner. The pacemaker IPG 140 is therefore illustrated as either a programmable, single chamber atrial or ventricular IPG operating in an atrial demand or ventricular demand pacing mode.

A temporary operation (or telemetry operation) is established with the IPG 140 by application of a permanent magnet 116 by the physician or other medical care provider to the patient's skin over the IPG 140 according to protocols that are particular to the IPG 140. In this respect, the normal demand pacing mode is suspended to allow for the determination of programmed pacing rate, pulse width and battery voltage in a manner well known in the art. In certain pacing IPGs described in the above-referenced '188 and '342 patents, a programming/interrogation protocol can also be followed that simply employs repeated applications of a discrete magnet 116 over the magnetically actuated MEM switch 130 to make programming changes and interrogate the IPG memory.

FIGS. 1 and 2 also show the more typical manner of programming and interrogating an IMD 100/IPG 140 using a sophisticated programmer 110 and programming head 150 placed over the IMD 100/IPG 140 to commence a telemetry session of uplink and downlink telemetry transmissions. The permanent magnet 116 within the programming head 150 of programmer 110 causes the MEM switch 130 to close and establish a communication link that enables a telemetry session. The programmer 110 is preferably a MEDTRONIC® Model 9790 programmer and communicates with the IMD 100 through a telemetry link between telemetry antenna 112 in programming head 150 and telemetry antenna 134 within the IPG 140 in a manner well known in the art.

A great many telemetry schemes have been employed and proposed by the assignee, Medtronic, Inc., and others for communications between IMDs and external monitors or programmers. The Model 9790 programmer 110 communicates with the IMD 100/IPG 140 through short range telemetry transmissions employing a 175 KHz RF carrier and close physical coupling of magnetic fields encompassing the RF telemetry antennae 112 and 134. For convenience of description, the preferred embodiment is described as follows using short range RF downlink telemetry (DT) and uplink telemetry (UT) transmission, but the invention and following claims are not be interpreted as so limited. Similarly, the terms "telemeter", "telemetry transmission" and the like are intended to embrace any such action and manner of communicating and conveying data and commands between the IMD 100 or IPG 140 and any external monitoring device or programmer 110 in the UT direction and the DT direction.

Thus, FIGS. 1 and 2 also depict manners of communicating with an IMD 100 when implanted in a patient's body 10 through the use of the externally applied magnetic field and a magnetic field responsive MEM switch 130 within the IMD 100. The MEM switch 130 may be normally closed or normally open and be opened or closed by the externally applied magnetic field. For simplicity of description and illustration, MEM switch 130 is described and depicted herein as normally open.

As shown in FIG. 1, the MEM switch 130 is coupled with a MEM switch circuit 120 that provides a "switch closed" control signal SC to the microcomputer-based control and timing system 102 when a STROBE signal is received from the microcomputerbased control and timing system 102 and the MEM switch 130 is closed. The strobe signal can be a system clock (CLK) signal or a periodically generated signal that relates to an IMD operating function, e.g., the timing of a pacing escape interval in the case of a pacing system, and is synchronized with the CLK signal. The microcomputer-based control and timing system 102 processes the SC signal to initiate a temporary change in an operating mode and/or parameter value, to deliver a therapy or commence a monitoring function, or to enable a telemetry session as long as the magnetic field maintains the MEM switch 130 closed or for a predetermined time period following generation of the SC signal. As described above, the magnetic field is provided by a permanent magnet 116 (or an electromagnet) which may be a discrete magnet or may be incorporated into the programming head 150 of programmer 110 that is typically employed in current programming and interrogation protocols between IMD 100 and external programmer 110.

Figures 5, 6:
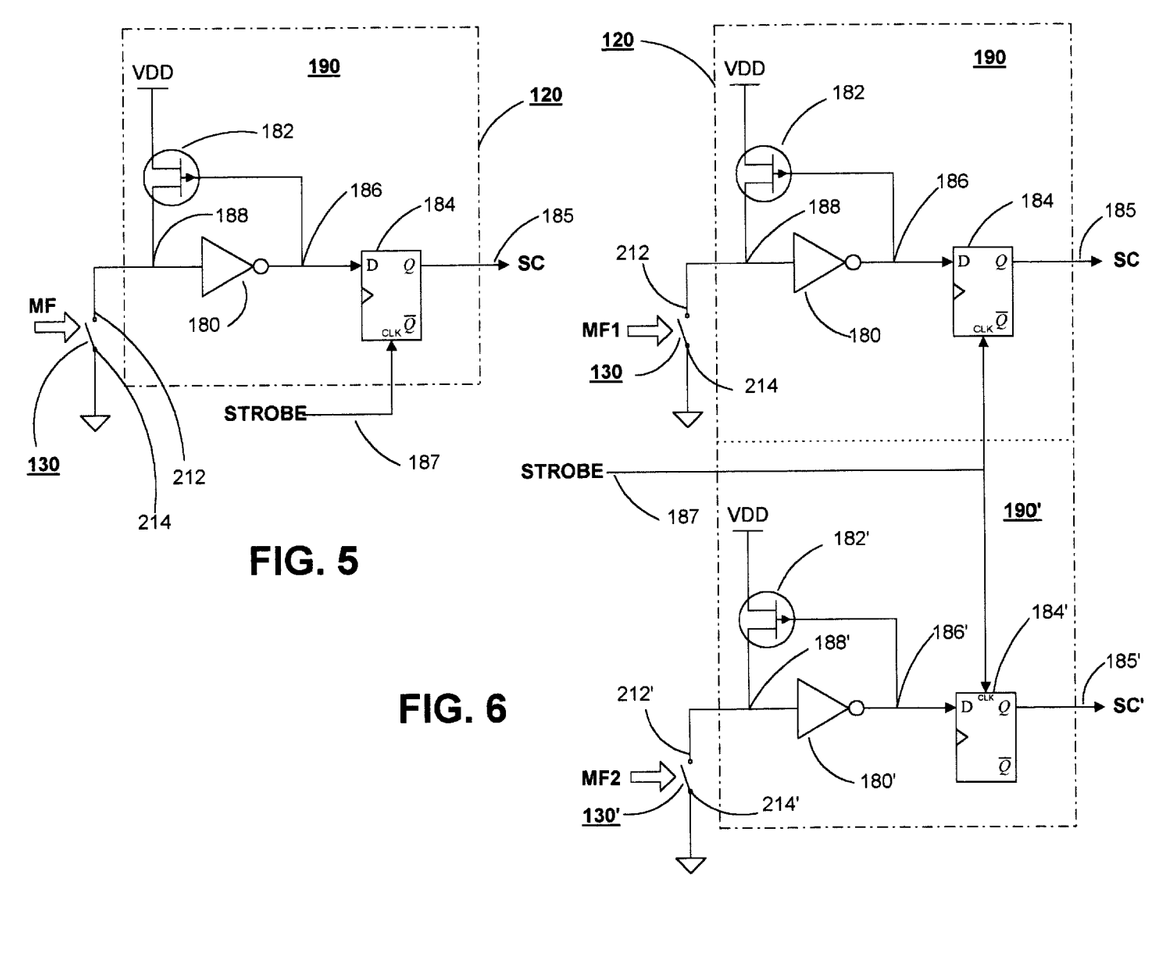
FIG. 5 is a simplified schematic diagram illustrating the functional interconnection of a magnetic field responsive MEM switch with a strobe signal for detecting and responding to the closure and re-opening of the contacts of the MEM switch.
FIG. 6 is a simplified schematic diagram illustrating the use of first and second MEM switches responsive to differing applied magnetic field poles or strengths in the manner depicted in FIG. 5.

In accordance with the present invention, one or more magnetic field responsive or actuated MEM switch 130 is incorporated into an IC of the IMD 100 or IPG 140 operating through the MEM switch circuit 130 depicted in FIG. 5, for example. In accordance with FIGS. 6 and 7, two or more MEM switches can be provided that selectively respond to externally applied north and south pole fields and/or to differing magnetic field intensities to cause the IMD to selectively respond and operate in separate prescribed operating modes.

Each such magnetic field actuated MEM switch 130 may be fabricated by a variety of techniques and may take a variety of forms. In one approach, semiconductor batch fabrication techniques are employed to achieve what is in effect three-dimensional micromachining of single-crystal and polycrystalline silicon and silicon dielectrics into beam or membrane structures that are undercut and suspended in space over a trench or hole or pit etched in the substrate. A temporary structure known alternatively as a release layer or as a sacrificial layer allows moving parts to be formed by self-registered casting methods, with subsequent selective etching to remove the sacrificial layer. Since micromachining originated from the technology of silicon integrated circuit processing, low-temperature $SiO_2$ is commonly employed as the sacrificial layer material. Micromachining of silicon substrates and low-temperature $SiO_2$ through the use of etchants and doping to control etching and thin film deposition of conductive layers allow fabrication of MEM switches completely from single crystal silicon. MEM silicon sensors or switches take advantage of precision photolithography and batch processing to facilitate miniaturization and reduce fabrication costs. Only selective deposition and removal of materials on a substrate add to conventional CMOS fabrication processes. One or more such MEM silicon sensors or switches can be incorporated into an IC substrate with other CMOS circuitry. Descriptions of micromachining techniques and various etchants are described by G. T. A. Kovacs et al. in "Bulk Micromachining of Silicon" (*Proc. of the IEEE*, vol. 86, no. 8, 8/98, pp. 1536–1551), for example. The fabrication and characteristics of a simplified, electrically actuated, cantilever beam switch is described in "Electrostatically actuated micromechanical switches using surface micromachining" retrieved from http://twww.ece.neu.edu/edsnu/zavracky/mfl/programs/relaylrelay.html (2/14/00). The form and fabrication of magnetically actuated suspended membrane and bridge MEM switches are also described in U.S. Pat. Nos. 5,778,513 and 5,475,353.

Figure 3:
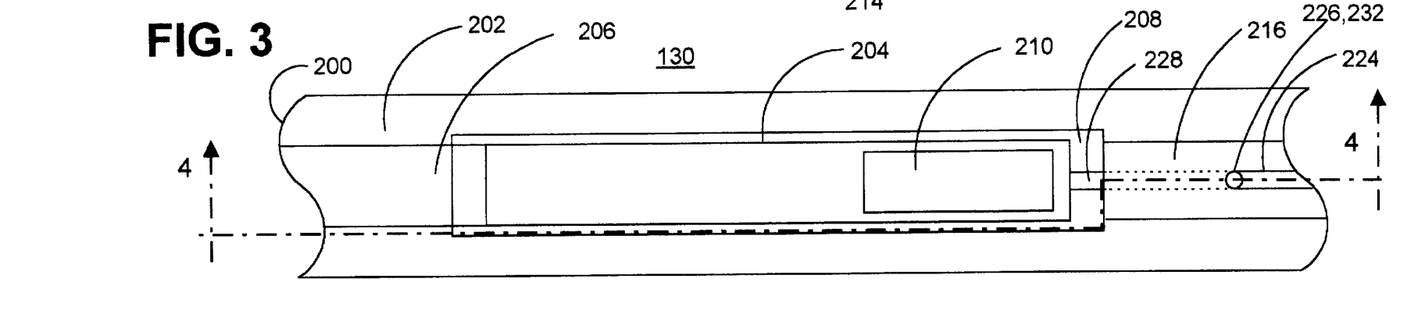
FIG. 3 is a top view of an exemplary cantilevered beam, magnetic field responsive MEM switch formed by bulk micromachining that can be employed in the exemplary IMD of FIGS. 1 and 2.
Figure 4:
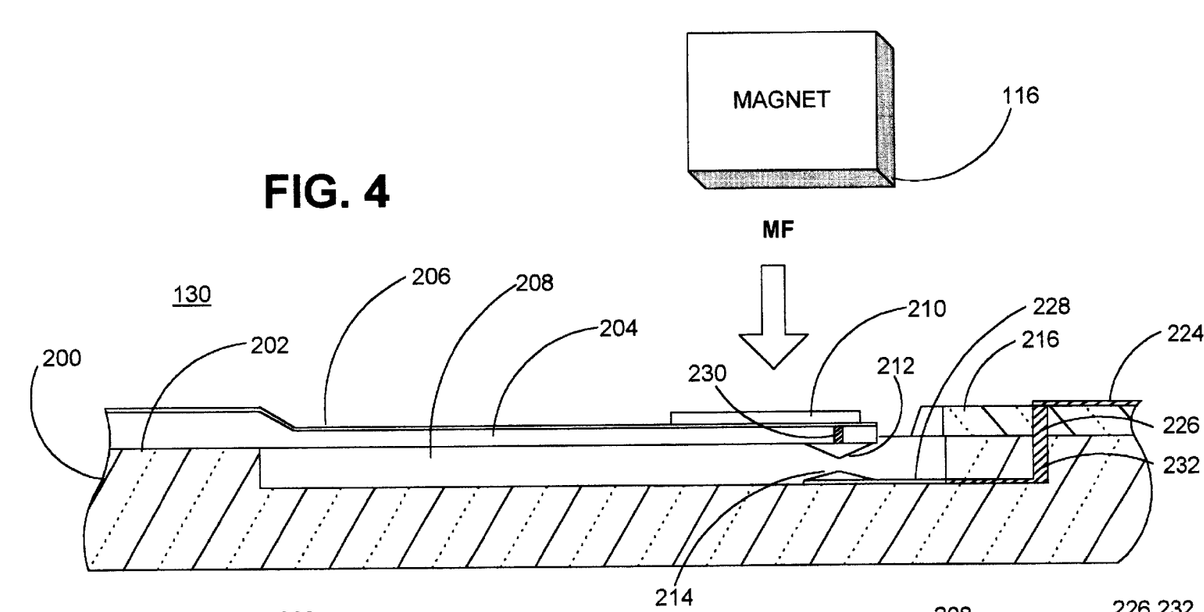
FIG. 4 is a side view in partial cross-section taken along lines 4—4 of FIG. 3 of the cantilevered beam MEM switch in relation to an externally applied magnetic field that can be employed in the exemplary IMD of FIGS. 1 and 2.

FIGS. 3 and 4 illustrate an exemplary cantilevered beam, magnetically actuated MEM switch 130 fabricated to be suspended over trench or well 208 etched in silicon substrate 200 in relation to the magnetic field of an externally applied magnet 116 that can be employed to close (or open) the switch contacts 212 and 214. It will be understood that the suspension member 204, a cantilever beam in this illustrated example, the beam contact 212, and the substrate contact 214 may take any advantageous form. The suspension member 204 may alternatively be fabricated with a membrane or bridge suspension of the magnetically deflected beam contact 212.

The substrate 200 is preferably a <110> or <100> orientation wafer that allows for anisotropic wet etching as described in the above-referenced fabrication articles and patents. The substrate 200 is first formed of silicon with internal metallizations and vias. An elongated polysilicon ($SiO_2$) layer 216 formed on the substrate 200 at the location where a MEM switch 130 is to be fabricated. The substrate 200 and polysilicon layer 216 are etched to form the well 208 and the suspension member 204 suspended over it. A via 230 is also formed through the polysilicon layer 216 at the free end of suspension member 204 to make electrical connection with the beam contact 212, and a metallization conductor 206 is formed along the upper surface of the suspension member 204. A second metallization conductor 224 is formed on the surface of the polysilicon layer 216 that extends to a via 226 extending therethrough to a further via 232 in the silicon substrate. The via 232 is coupled with a metallization trace 228 extending to the fixed substrate contact 214. The beam and fixed contacts 212 and 214 are formed against the via 230 and trace 228, respectively.

The beam switch contact 212 and substrate switch contact 214 are preferably formed by sputtering or evaporation of one of platinum, aluminum, gold, nickel, tantalum, titanium and alloys thereof upon the via 230 and trace 228, respectively. Chemical vapor deposition (CVD), low pressure chemical vapor deposition (LPCVD) and plasma enhanced chemical vapor deposition (PECVD) techniques may be employed. The traces, vias and surface metallization conductors are preferably formed of aluminum, copper, gold and alloys thereof.

The switch contacts 212 and 214 are normally separated apart as depicted in FIG. 4 to provide a normally open switch, although it will be understood that they may be normally in contact with one another to provide a normally closed switch. A ferromagnetic layer 210 is deposited upon the upper surface of the suspended end of cantilever beam 204 or applied as a dopant to the semiconductor material of cantilever beam 204. The magnetic field of a magnet 116 is brought into proximity with MEM switch 130 can either attract or repel the ferromagnetic layer 210 and beam 204, depending upon the magnetic field polarity and the ferromagnetic material composition of ferromagnetic layer 210. In the depicted relationship of the applied magnetic field, the properly applied magnetic field repels the ferromagnetic layer 210 and cantilever beam 204 so that the switch MEM 130 is closed by mutual contact of the switch contacts 212 and 214.

The MEM switch 130 can be configured to require a certain threshold magnetic field intensity to effect closure by tailoring the stiffness and length of the suspension element, e.g., the cantilever beam 204, the type, surface area and thickness of the ferromagnetic layer 210, and the separation distance between the contacts 212 and 214. Multiple MEM switches having differing magnetic field intensity thresholds can be fabricated into a single substrate 200 so that the MEM switch or switches that are closed depends on the strength of the applied magnetic field.

If the layer 210 is formed of a relatively soft ferromagnetic material e.g., $Ni_{80}Fe_{20}$, then the MEM switch contacts 212 and 214 are closed when a magnetic field of sufficient strength and of either north (N) or south (S) polarity is applied by magnet 116, for example. But, the MEM switch 130 can be made selectively responsive to the applied magnetic field of N polarity or S polarity so that only the proper applied magnetic field polarity will repel the ferromagnetic layer 210 and beam 204 to close the MEM switch contacts 212 and 214. Magnetically hard, Permalloy materials may be employed that are permanently magnetized to a predetermined magnetic field orientation at the time of manufacture of the MEM switch 130.

In the actual environment of use as depicted in FIGS. 1 and 2, it is necessary to detect the closure and re-opening of the MEM switch contacts 212 and 214 caused by the applied and withdrawn magnetic field of the external discrete or programming head magnet 16. The magnetic field is applied by the medical care provider or patient for a time that depends on the operation or response that it is intended to cause in the IMD. The beam contact 212 and conductor 206 is at a common supply voltage representing a HIGH logic level when substrate 200 and substrate contact 214 is electrically at system common ground representing a logic LOW level. The logic level transition is from HIGH to LOW upon closure of the contacts 212 and 214 and from LOW to HIGH on re-opening of the contacts 212 and 214. These transitions associated with closure and re-opening of the switch contacts 212 and 214 are not necessarily (but may coincidentally) synchronized with the system clock transitions that govern typically clocked operations of the IMD operating system depicted in FIG. 1. The HIGH to LOW and LOW to HIGH signal level transitions may be electrically noisy or intermittent or at a slew rate that is not recognized or causes confusion in the particular CMOS circuitry that the switch 130 would be coupled with to effect the change in operating mode or delivery of a therapy or enabling a telemetry session, etc. Therefore, it is desirable to be able to detect the HIGH or LOW state of the beam contact 212 when the signal level is stable and to not rely of the logic level transition of the switch itself.

FIG. 5 is a simplified schematic diagram illustrating the functional interconnection of a magnetic field responsive MEM switch 130 with a strobe signal for detecting and responding to the closure and re-opening of the contacts 212 and 214 of the MEM switch. In FIG. 5, the switch contact 214 is coupled to system ground, and switch contact 212 is coupled to a supply voltage VDD through a minimal die size p-channel FET 182 and is coupled to the input of minimal die size inverter 180 at node 188. The output of inverter 180 (at node 186) is coupled to the gate of FET 182 and the D input of D-type flip-flop 184. While switch 130 is open, node 188 is HIGH due to conduction of FET 182, and node 186 is LOW due to inverter 180. No current is consumed to maintain node 188 HIGH and 186 LOW due to the high gate to source-drain resistances of FET 182 and the FETs forming inverter 180.

The STROBE signal is periodically applied as described above to the dock (CLK) input of D-type flipflop 184, and the Q output of D-type flip-flop 184 is set to the logic level found at node 186. The strobe signal is generated by or synchronized to the system dock signal CLK The Q output is therefore at a logic LOW level as long as the MEM switch 130 is open. The logic HIGH SC (switched dosed) output signal is therefore not produced as long as the MEM switch 130 is open.

But, MEM switch 130 doses when an applied magnetic field MF exceeds the switching threshold, and the voltage logic levels at nodes 188 and 186 reverse to LOW and HIGH, respectively. Magnetically actuated MEM switch 130 may be configured and fabricated to respond to a particular polarity magnetic field or a magnetic field of either N or S polarity exceeding, in either case, a magnetic field strength threshold level. The STROBE signal following or contemporaneous with MEM switch closure and the resulting HIGH logic level at node 186 causes the Q output SC of D-type flipflop 184 to switch HIGH on line 185. The logic HIGH SC output signal on line 185 is provided to the microcomputerbased control and timing system 102 of FIG. 1 in synchrony with the STROBE signal. The Q output remains at the logic HIGH level as long as the MEM switch 130 is closed and is switched back to the logic LOW level when the MEM switch 130 is re-opened and a STROBE signal occurs.

The MEM switch circuit 120 thereby provides the SC signal having proper synchronization (both upon its start and end) with the system CLK signal and suitable rise time and fall time signal waveform. The inverter 180 also provides clean transitions between HIGH and LOW logic levels at node 186 in response to opening and closing of the switch contacts 212 and 214 that ensures reliable response by the D-type flip-flop 184.

FIG. 6 is a simplified schematic diagram illustrating the use of first and second MEM switches 130 and 130' responsive to differing applied magnetic field poles or strengths to provide first and/or second switch closed signals SC and SC' to the microcomputerbased control and timing system 102 of FIG. 1. The MEM switches 130 and 130' are coupled to respective signal processing circuits 190 and 190' of the type described above in reference to FIG. 5 within the MEM switch circuit 120.

MEM switch 130 closes when a first magnetic field MF1 is applied, and the signal SC is generated by the first signal processing circuit 190 upon the STROBE signal following or contemporaneous with switch closure. MEM switch 130' closes when a second magnetic field MF2 is applied, and the signal SC' is generated by the second signal processing circuit 190' upon the STROBE signal following or contemporaneous with switch closure.

If the MEM switches 130 and 130' are not polarity sensitive, then a first field strength threshold is defined to close MEM switch 130, and a second field strength threshold, greater than the first field strength threshold, for example, is defined to close MEM switch 130'. In this case, MF1 simply must exceed the first field strength threshold to close MEM switch 130, and MF2 must exceed the second field strength threshold to close both MEM switches 130 and 130'.

But, if the MEM switches 130 and 130' are polarity sensitive, then only one is closed at a time. A first N polarity field strength threshold is defined to close MEM switch 130, and a second S polarity field strength threshold, different or the same as the first field strength threshold, for example, is defined to close MEM switch 130'.

Figure 7:
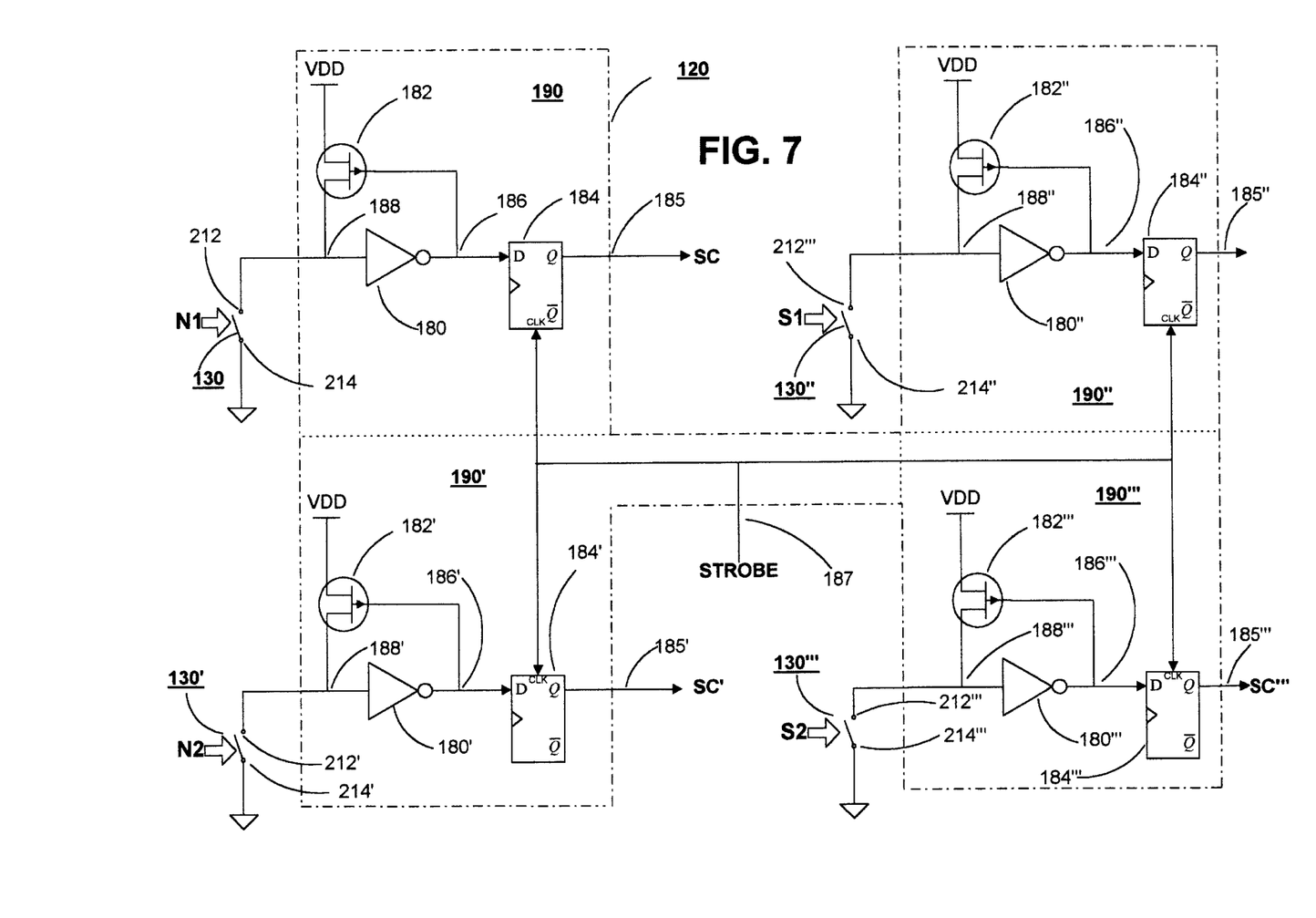
FIG. 7 is a simplified schematic diagram illustrating the use of four MEM switches each responsive to differing applied magnetic field poles and field strengths in the manner depicted in FIG. 5.

FIG. 7 is a simplified schematic diagram illustrating the use of four MEM switches 130, 130', 130", and 130"" each coupled to respective signal processing circuits 190, 190', 190", and 190''', respectively. Each one of signal processing circuits 190, 190', 190", and 190''' provide a respective one of signals SC, SC', SC", and SC''' to microcomputer-based control timing system 102 when one of respective MEM switches 130, 130', 130", and 130"" are closed in response to respective applied magnetic fields N1, N2, S1, and S2. In this way one of four possible logic HIGH signals SC, SC', SC", and SC''' are generated on lines 185, 185', 185" and 185''', respectively.

It will be understood that the separate, parallel signal processing circuits 190, 190', 190", and 190''' could be combined. It will also be understood that the MEM switches 130, 130', 130", and 130"" can be fabricated to be closed in response to respective applied magnetic fields that are of the same polarity but of four separate field strengths. Or the MEM switches 130, 130', 130", and 130"" can be fabricated to be closed in response to respective applied magnetic fields of any polarity but of four separate field strengths. FIG. 7 is merely exemplary of one of a wide number of combinations of pluralities of MEM switches sensitive to the same or differing polarity applied magnetic fields at specified field intensity or strength thresholds that can be employed in accordance with the teachings of the present invention.

Each one of the plurality of switch dosed signals, e.g., signals SC, SC', SC", and SC''', can be employed to initiate a particular change in operating mode or parameter value. The provision of one or more or all of the signals SC, SC', SC'', and SC''' can be employed to enable a programming sequence using the programmer 110 coupled to the programming head 150, having a permanent magnet 116 providing the requisite magnetic field to effect closure. At other times, separate magnets 116 may be applied to the patients skin to effect closure of one or more of the MEM switches, e.g. switches 130, 130', 130'' and 130''', to cause the IMD to change operating mode or a parameter value.

Moreover, combinations of closures of one or more of the MEM switches, e.g. switches 130, 130', 130'' and 130''', can be employed using the discrete magnets alone to cause the IMD to change operating mode or a parameter value and to effect programming and uplink telemetry in the manner described in the above-referenced '188 and '342 patents.

The incorporation of multiple MEM switches, e.g. switches 130, 130', 130'' and 130''', can be advantageously made due to the simple fabrication thereof into a minute space of a CMOS substrate along with CMOS circuitry.

Other fabrication techniques, e.g. surface machining and LIGA (Lithographie, Galvanoformung, Abformung), can be used to form the magnetically actuated MEM switches on a silicon substrate for CMOS circuitry of the IMD.

Silicon is not the only substrate material that has been employed in micromachining, and other materials and micromachining techniques described in the art could be used to form the magnetically actuated MEM switch 130 employed in the IMDs of the present invention. The formation of bulk micromachined and surface micromachined cantilever beams employing piezoelectric PZT thin films for MEM accelerometers and relays is described in U.S. Pat. No. 5,914,907. Micromechanical properties of sputtered molybdenum are discussed in the paper by Richard B. Brown, Muh-Ling Ger and Tri Nguyen, "Characteristics of Molybdenum Thin Films for Micromechanical Structures" *Proc. IEEE Microelectromechanical Systems, An Investigation of Microstructures, Sensors, Actuators, Machines and Robots*, Napa Valley, Calif., Feb 11–14, 1990 (IEEE Cat. No. 90CH2832-4). Brown et al. also suggest use of sputtered aluminum as a sacrificial layer in order to increase etch selectivity and to avoid cracks in molybdenum cantilever beams due to compressive forces originating in an $SiO_2$ release layer. In addition, the magnetically actuated MEM switch 130 can be fabricated employing high density interconnect (HDI) technology in the manner disclosed in U.S. Pat. No. 5,454,904.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims.

What is claimed is:

1. An implantable medical device (IMD) to provide therapy delivery and/or monitoring for a patient, the IMD further comprising:

a control and timing circuit implementing an IMD operating mode;

a microelectromechanical switch having a fixed contact, a moveable suspension member, a ferromagnetic layer formed on the suspension member, a moveable switch contact formed on the suspension member and disposed over the fixed contact, wherein the moveable switch contact is normally in a first position and assumes a second position when a predetermined magnetic field strength is applied to the ferromagnetic layer and causes a deflection of the suspension member:

a switch processing circuit producing a switch signal responsive to the assumption of the second position by the moveable switch contact; and wherein the control and timing circuit implements an IMD operating mode in response to the switch signal.

2. The IMD of claim 1, wherein the IMD control and timing circuit responds to the switch signal by establishing an IMD telemetry operating mode.

3. The IMD of claim 2, wherein the IMD has stored information and the IMD telemetry operating mode accesses the stored information in the IMD.

4. The IMD of claim 1, wherein the IMD has a programmed operating mode and the control and timing circuit implements an operating mode in accordance with the programmed operating mode in response to the switch.

5. The IMD of claim 1, wherein the IMD has programmed parameter values and the control and timing circuit implements an operating mode in accordance with the programmed parameter values in response to the switch signal.

6. The IMD of claim 1, wherein the control and timing circuit, the switch processing circuit, and the microelectromechanical switch are on a common integrated circuit substrate.

7. The IMD of claim 1, wherein:

the control and timing circuit periodically generates a strobe signal; and the switch processing circuit provides the switch signal when the strobe signal is generated, the predetermined magnetic field strength is applied to the ferromagnetic layer, and deflection of the suspension member places the moveable switch contact in the second position with respect to the fixed switch contact.

8. An implantable medical device (IMD) having a hermetically sealed enclosure and adapted to be implanted in a patient's body and to provide a therapy delivery and/or monitoring, the IMD further comprising:

a control and timing circuit implementing an IMD operating mode;

a first microelectromechanical switch having a fixed contact, a moveable suspension member, a ferromagnetic layer formed on the suspension member, a first moveable switch contact formed on the suspension member and disposed over the fixed contact, wherein the first moveable switch contact is normally in a first position and assumes a second position when a predetermined magnetic field strength is applied to the ferromagnetic layer and causes a deflection of the suspension member;

a first switch processing circuit producing a first switch :signal responsive to the assumption of the second position by the moveable switch;

a second first microelectromechanical switch having a fixed contact, a second moveable suspension member, a ferromagnetic layer formed on the suspension member, a moveable switch contact formed on the suspension member and disposed over the fixed contact, wherein the second moveable switch contact is normally in a first position and assumes a second position when a predetermined magnetic field strength is applied to the ferromagnetic layer and causes a deflection of the suspension member;

a second switch processing circuit producing a second switch signal responsive to the assumption of the second position by the moveable switch; and wherein the control and timing circuit in response to the first switch signal implements a first IMD operating mode and in response to the second switch signal implements a second IMD operating mode.

9. The IMD of claim 8, wherein the control and timing circuit responds to one or both of the first and second switch signals by establishing an IMD telemetry operating mode.

10. The IMD of claim 9, wherein the IMD has stored information and the IMD telemetry operating mode accesses the stored information in the IMD.

11. The IMD of claim 8, wherein the IMD has a programmed operating mode and the control and timing circuit implements an operating mode in accordance with the programmed operating mode in response to one of the first and second switch signals.

12. The IMD of claim 8, wherein the IMD has programmed parameter values and the control and timing circuit implements an operating mode in accordance with programmed parameter values in response to one of the first and second switch signals.

13. The IMD of claim 8, wherein the control and timing circuit, the first and second switch processing circuits, and the first and second microelectromechanical switches are on a common integrated circuit substrate.

14. The IMD of claim 8, wherein:
the control and timing circuit periodically generates a first strobe signal;
the first switch processing circuit provides the first switch signal when the strobe signal is generated, the first predetermined magnetic field characteristic is applied to the ferromagnetic layer, and deflection of the suspension member places the moveable switch contact in the second position with respect to the fixed switch contact; and
the second switch processing circuit provides the second switch signal when a second strobe signal is generated, the second predetermined magnetic field characteristic is applied to the ferromagnetic layer, and deflection of the suspension member places the moveable switch contact in the second position with respect to the fixed switch contact.

15. The IMD of claim 14, wherein the first predetermined magnetic field characteristic is a first predetermined magnetic field strength, and the second predetermined magnetic field characteristic is a second predetermined magnetic field strength.

16. The IMD of claim 14, wherein the first predetermined magnetic field characteristic is a first predetermined magnetic field polarity, and the second predetermined magnetic field characteristic is a second predetermined magnetic field polarity.

17. The IMD of claim 8, wherein the first predetermined magnetic field characteristic is a first predetermined magnetic field strength, and the second predetermined magnetic field characteristic is a second predetermined magnetic field strength.

18. The IMD of claim 8, wherein the first predetermined magnetic field characteristic is a first predetermined magnetic field polarity, and the second predetermined magnetic field characteristic is a second predetermined magnetic field polarity.

* * * * *